United States Patent
Kremer et al.

(10) Patent No.: US 9,921,177 B2
(45) Date of Patent: Mar. 20, 2018

(54) METHOD OF MEASURING AND MONITORING CONDUCTIVITY IN-SITU IN HIGH TEMPERATURE AQUEOUS SYSTEMS

(71) Applicant: Baker Hughes Incorporated, Houston, TX (US)

(72) Inventors: Lawrence N. Kremer, The Woodlands, TX (US); Sidney A. Dunn, Lake Charles, LA (US); David N. Fulmer, Missouri City, TX (US); Regis R. Rumpf, Mars, PA (US)

(73) Assignee: Baker Hughes, a GE company, LLC, Houston, TX (US)

(*) Notice: Subject to any disclaimer, the term of this patent is extended or adjusted under 35 U.S.C. 154(b) by 104 days.

(21) Appl. No.: 14/725,821

(22) Filed: May 29, 2015

(65) Prior Publication Data

US 2015/0362452 A1    Dec. 17, 2015

Related U.S. Application Data

(60) Provisional application No. 62/012,816, filed on Jun. 16, 2014.

(51) Int. Cl.
*G01N 27/30* (2006.01)
*F22B 37/00* (2006.01)

(52) U.S. Cl.
CPC ............ *G01N 27/308* (2013.01); *F22B 37/00* (2013.01)

(58) Field of Classification Search
None
See application file for complete search history.

(56) References Cited

U.S. PATENT DOCUMENTS

| | | | |
|---|---|---|---|
| 4,455,530 A * | 6/1984 | Lee | G01N 27/048 324/446 |
| 8,105,469 B2 | 1/2012 | Whitehead et al. | |
| 2004/0221796 A1* | 11/2004 | Swain | C23C 16/274 117/84 |
| 2012/0132468 A1 | 5/2012 | Scott et al. | |
| 2012/0192949 A1 | 8/2012 | Petzoldt | |
| 2013/0239997 A1 | 9/2013 | Barber | |
| 2013/0284913 A1 | 10/2013 | Pinappu et al. | |
| 2013/0327640 A1 | 12/2013 | Mollart et al. | |

FOREIGN PATENT DOCUMENTS

GB      2489106 A   *   9/2012   ........... G01N 27/308

OTHER PUBLICATIONS

Mettler Toledo, "Industrial Boiler Blowdown Control Using Conductivity", Application Note No. AN-0119, revised last on Dec. 2008, 3 pages.*
A. Furmanov, "Temperature of Steam in a Tubine", from "The Physics Factbook" (URL: https://hypertextbook.com/facts/2003/AlanFurmanov.shtml), 2003, 1 page.*
DIAFILM EA, Enabling New Electroanalytical Applications, Sensing & Detecting, Element Six.
European Patent Office, International Search Report and Written Opinion, International Application No. PCT/US2015/033298, dated Aug. 28, 2015.
Gray, David M., A Comprehensive Look at Conductivity Measurement in Steam and Power Generation Waters, 67th Annual Intl Water Conf., Engineers Society of Western Pittsburgh, PA, Oct. 2008.
Gustafon, et al., Determination of Total Dissolved Solids in Water Electrical Conductivity, Industrial and Engineering Chemistry, Analytical Edition, Jul. 15, 1939, pp. 355-357.
Hutton et al., Examination of the Factors Affecting the Electrochemical Performance of Oxygen-Terminated Polycrystalline Boron-Doped Diamond Electrodes, Anal. Chem., pubs.acs.org/doi/abs/10.1021/ac401042t, 2013.
Mollart, et al., Downhole Sensors Based on Synthetic Diamond, Element Six Ltd.
Thornton, Industrial Boiler Blowdown Control, Using Conductivity, Application Note AN-0119, Leading Pure Water Analytics, Dec. 1, 2008.

* cited by examiner

*Primary Examiner* — J. Christopher Ball
(74) *Attorney, Agent, or Firm* — Jones Delflache LLP

(57) ABSTRACT

Monitoring of conductivity within a steam generating system may proceed in real time and without interruption of the steam generating system by use of a boron doped diamond based electrochemical band sensor placed within the steam generating system. The boron doped diamond based electrochemical band sensor has a diamond body and a plurality of boron doped diamond band electrodes disposed within the diamond body. At least a portion of each of the plurality of boron doped diamond band electrodes is doped with boron to provide metallic conduction.

27 Claims, No Drawings

METHOD OF MEASURING AND MONITORING CONDUCTIVITY IN-SITU IN HIGH TEMPERATURE AQUEOUS SYSTEMS

This application claims the benefit of U.S. patent application Ser. No. 61/012,816, filed on Jun. 16, 2014 which is herein incorporated by reference.

FIELD OF THE DISCLOSURE

The disclosure relates to a method of measuring and monitoring the conductivity of aqueous based fluids at in-situ conditions using a boron doped diamond based electrochemical band sensor.

BACKGROUND OF THE DISCLOSURE

Steam generating systems, such as boilers, are commonly used in industrial, institutional and multi-unit residential facilities including petrochemical plants, oil refineries, power generation stations, hotels, schools, etc. Steam, formed from water, in the steam generating system is distributed throughout the facility to provide heat for use in comfort, processing, power generation, etc. Upon condensation, water is typically returned to the steam generator (or boiler) for efficiency.

Steam generating systems are designed to operate such that the condensate has conductivity, pH, and temperature within a targeted range. Typically, such systems are operated at temperatures from 500° F. to about 900° F. Deviations in conductivity, pH, and temperature of condensate from the targeted range are indicative of problems within the steam generating system. Such problems may include mineral scale, carbonic corrosion, and thermal fatigue. These problems may result in costly maintenance and repairs to the steam generating system. Thus, continual monitoring of conductivity as a measurement of water quality is required.

Currently, there is no method of measuring conductivity in steam generating systems without cooling down the water. Typically, water must be cooled down to a temperature no greater than 100° F. in order to protect the probe used in measuring conductivity. A more efficient method of measuring conductivity which provides the ability for real time or near real time monitoring is desired.

It should be understood that the above-described discussion is provided for illustrative purposes only and is not intended to limit the scope or subject matter of the appended claims or those of any related patent application or patent. Thus, none of the appended claims or claims of any related application or patent should be limited by the above discussion or construed to address, include or exclude each or any of the above-cited features or disadvantages merely because of the mention thereof herein.

SUMMARY OF THE DISCLOSURE

In an embodiment of the disclosure, a method of monitoring conductivity in a steam generating system is provided. In this method, conductivity of a fluid is measured in a steam generating system by contacting the fluid with a boron doped diamond based electrochemical band sensor. The boron doped diamond based electrochemical band sensor has a diamond body and a plurality of boron doped diamond band electrodes disposed within the diamond body. The conductivity is measured by applying voltage to the boron doped diamond based electrochemical band sensor at a temperature from about 250° F. to 1200° F., in most cases between from about 500° F. to about 900° F.

In another embodiment of the disclosure, a method of monitoring conductivity in real time in a steam generating system is provided. Operation of the steam generating system is not interrupted during the real time monitoring. The monitoring is conducted by contacting fluid in a steam generating system with a boron doped diamond based electrochemical band sensor. The boron doped diamond based electrochemical band sensor has a diamond body and a plurality of boron doped diamond band electrodes disposed within the diamond body. The conductivity is measured by applying voltage to the boron doped diamond based electrochemical band sensor.

In another embodiment, a method of monitoring conductivity in a hydrothermal liquefaction unit during hydrothermal liquefaction of a water based slurry is provided. The hydrothermal liquefaction unit is operated at a temperature between from about 575° F. to about 950° F. and at a pressure sufficient to maintain the water in the liquid phase. In the method, a water based slurry is contacted with a boron doped diamond based electrochemical band sensor in the hydrothermal liquefaction unit. The boron doped diamond based electrochemical band sensor has a diamond body and a plurality of boron doped diamond band electrodes disposed within the diamond body. Conductivity of the water based slurry is measured at the operating temperature by applying voltage to the boron doped diamond based electrochemical band sensor.

DETAILED DESCRIPTION OF THE PREFERRED EMBODIMENTS

Characteristics and advantages of the present disclosure and additional features and benefits will be readily apparent to those skilled in the art upon consideration of the following detailed description of exemplary embodiments of the present disclosure. It should be understood that the description herein, being of example embodiments, are not intended to limit the claims of this patent or any patent or patent application claiming priority hereto. Many changes may be made to the particular embodiments and details disclosed herein without departing from such spirit and scope.

As used herein and throughout various portions (and headings) of this patent application, the terms "disclosure", "present disclosure" and variations thereof are not intended to mean every possible embodiment encompassed by this disclosure or any particular claim(s). Thus, the subject matter of each such reference should not be considered as necessary for, or part of, every embodiment hereof or of any particular claim(s) merely because of such reference. Also, the terms "including" and "comprising" are used herein and in the appended claims in an open-ended fashion, and thus should be interpreted to mean "including, but not limited to . . . ."

The conductivity of a fluid in a steam generating system may be measured in-situ by use a boron doped diamond based electrochemical band sensor as described herein. The sensor may be used to measure conductivity at in-situ conditions at temperatures from about 250° F. to as high as 900° F., in some cases as high as 1100° F. and in other cases as high as 1200° F. For instance, in a very low pressure boiler, the temperature may be about 250° F. and in a supercritical boiler about 700° F.

In light of the ability to measure conductivity at such elevated temperatures, cooling the steam generating system down to a lower temperature is not necessary. As such, conductivity may be monitored in real time without interrupting operation of the steam generating system when the boron doped diamond based electrochemical band sensor is used. Since the method discussed herein provides a means for monitoring conductivity in real time at operation conditions, costs may be reduced.

The use of boron doped diamond based electrochemical band sensors thus facilitates boiler blowdown since water is only removed from the boiler on an "as required" basis. In other words, by in-situ monitoring of conductivity of boiler water, water is only removed from the steam generating system when solids contents (resulting, for instance, from scale formation, corrosion, carryover, etc) reach certain limits. In an embodiment therefore, the use of boron doped diamond electrochemical sensors within a steam generating system may be used to control the amount of unwanted solids within the boiler as well as to maintain steam quality.

By curtailing cool down of the steam generating system, a safer working environment is offered to operators as they are exposed less to handling of system elements.

The exact location of placement of the boron doped diamond based electrochemical band sensor within the steam generating system may be dependent on the design of the system as well as the stage in which conductivity is desired to be measured.

For instance, in an embodiment, the boron doped diamond electrode sensor may be placed within the boiler and conductivity measured within the boiler. Conductivity may also be measured by placement of the boron doped diamond based electrochemical band sensor in a take-off line, quick-opening valve, etc. Where the steam generating system is composed of multiples of such elements (such as multiple blowdown connections), the sensor may be placed within the element which is closest to the low water level. Alternatively, the sensor may be placed closest to the bottom of the steam drum.

Within the steam generating system, conductivity may be measured during condensation. Conductivity may also be measured during the generation of steam. By measuring the boiler water during operation of the steam generating system, the effect of dissolved solids within the operating system can be immediately determined.

In another embodiment, conductivity of the boiler water may be measured during blowdown. In this instance, the boron doped diamond based electrochemical band sensor may be placed in the blowdown line.

In another embodiment, conductivity may be measured within a flash tank or a heat exchanger during the recovery of blowdown water. Blowdown water typically has the same temperature and pressure as the boiler water. In this instance, the boron doped diamond based electrochemical band sensor may be placed within the flash tank or heat exchanger.

In a preferred embodiment, the boron doped diamond based electrochemical band sensor is placed inside of a probe. The probe may then be placed within the steam generating system as discussed herein.

In addition to the boron doped diamond based electrochemical band sensor, a pH probe may be placed within the steam generating system to measure the acidity and alkalinity of the condensate. Since acidity and alkalinity have a large effect on electrical conductivity, it is often necessary to neutralize the liquid before measuring conductivity. Further, a temperature probe to measure the temperature of the condensed steam may be placed within the steam generating system.

Further, a controller may be placed within the interior of the steam generating system in electrical communication with the sensor.

While a preferred embodiment is the use of the boron doped diamond based electrochemical band sensor in a boiler system, the sensors may also be employed in other steam generating systems. For instance, the sensor may be employed to measure conductivity within steam turbines. Fossil and nuclear steam turbines require substantial cool down time delays. A typical steam turbine requires a minimum of one week to cool down to ambient temperatures. This requires shutdown and outage disassembly which, in addition to being highly inefficient, is manpower extensive at a cost to the operator.

In another embodiment, the boron doped diamond electrochemical band sensors as described herein may be used to control hydrothermal liquefaction (HTL) units since such units typically operate with water-based slurries at temperatures between from about 575° F. to about 950° F. and sufficient pressure (typically about 20 MPa) to maintain the water in the liquid phase. Temperature and pressure are monitored during the process.

The processing is particularly applicable to wet biomass feedstocks, such as algae. The use of the boron doped electrochemical band sensors permits continuous testing for hydrothermal gasification of the feedstock. The use of the boron doped diamond electrochemical band sensor provides information on the progress of the reaction. The boron doped diamond electrochemical band sensor may be placed in the product recovery system, the preheater or the reactor itself. Typically, the reactor is a fixed bed reactor having a catalytic bed within the reactor. Alternatively, the boron doped diamond electrochemical band sensor may be placed in-line between the preheater and the reactor. In this situation, the boron doped diamond electrochemical band sensor may be placed within a high pressure vessel. When used in the hydrotreatment of biocrude, the boron doped diamond electrochemical band sensor may be placed at the point of separation of the aqueous byproduct stream from the treated stream.

In addition to HTL, the boron doped diamond electrochemical band sensors may be used to control any steam generating unit which operates at high temperatures as stated herein. Such steam generating units may include units used to enhance the recovery of oil such as steam assisted gravity drainage (SAGD), steam generating units for the enhancement of ethylene production or propylene production including steam cracking units, steam driven power plants, steam generating ammonia plants, etc.

The boron doped diamond electrochemical band sensors are polycrystalline and exhibit inert surface properties. As a result, the boron doped sensors neither react nor erode during electrochemical processes.

In addition, the boron doped sensors are resistant to fouling. As such, the boron doped diamond band sensors as described may be used in geothermal systems.

In a preferred embodiment, the boron doped diamond band sensors are represented by an array of high aspect ratio boron doped diamond electrodes which provide the structure of the band sensor. Connections are made to the bands by laser machining holes which pass from the back of an insulating wafer to the conducting bands. The high aspect ratio enables the boron doped diamond electrodes to exhibit a high length/width ratio at their sensing surface and thus provides improved sensing capabilities when compared with other boron doped diamond electrode arrangements.

Typically the boron doped diamond electrodes are a few microns in diameter, fabricated by applying a layer of $Si_3N_4$ or similar non-conductive material to the surface of the diamond and subsequently etching apertures into it to expose the diamond underneath.

Exemplary of such boron doped diamond based electrochemical band sensors are those commercially available from Element Six Limited as DIAFILM EA. Such materials are typically 0.4 mm in thickness and have an ohmic Ti:Pt:Au contact mellalization on their rear surface.

Boron doped electrodes are further disclosed in U.S. Pat. No. 8,105,469 and U.S. Patent Publication No. 2013/0327640, both of which are herein incorporated by reference. The diamond body of such sensors normally comprise a front "sensing" surface with the plurality of boron doped diamond band electrodes exposed at the sensing surface. The electrodes extend in an elongated manner across the sensing surface to form a plurality of bands. The boron doped diamond electrodes also extend back through the diamond body to a rear "electrical connection" surface which is opposed to the front sensing surface. This provides individual electrical connections to each of the plurality of boron doped diamond band electrodes. The boron doped diamond band electrodes form a substantially parallel array of boron doped diamond plates extending through the diamond body from the front sensing surface to the rear electrical connection surface. End caps of diamond material may be adhered to the diamond body adjacent opposing sides of the plurality of boron doped diamond band electrodes for insulating side edges of the plurality of electrodes from each other.

In a preferred embodiment, the front sensing surface is preferably substantially planar. By substantially planar it is meant that there are no large steps in height between the adjacent layers of boron-doped and intrinsic diamond on the front sensor surface. That is, such steps are equal to or less than 1 μm, 300 nm, 100 nm, 30 nm, 10 nm, 3 nm, 1 nm, 0.3 nm, or 0.1 nm. In particular, the size of any such step is a factor of 3, 10, 30, 100, 300, or 1000 smaller than the width of the electrode.

In addition to the boron doped diamond electrodes being linear extending over the sensing surface, the boron doped diamond electrodes may also be non-linear. For example, the front sensor surface may show macroscopic curvature, for example in the form of a segment of a sphere or more preferably a segment of a cylinder, to more usefully conform to the flow within the fluid being measured. Further, the sensor may comprise a parallel array of boron doped diamond band electrodes in a central region of the sensing surface and curved electrodes around a periphery of the sensing surface.

The diamond body and the plurality of boron doped diamond band electrodes may be formed by a single crystal of diamond material or a polycrystalline diamond material. Furthermore, the end caps may be formed by a single crystal diamond material or polycrystalline diamond material. Advantageously, a single crystal diamond material is utilized. The diamond material is preferably CVD (Chemical Vapor Deposited) diamond material. A functional coating layer may be provided at the sensing surface and a recess may be provided in which the functional material resides such that the sensing surface remains planar.

The aspect ratio at the sensing surface is high such that a length of a band electrode across the sensing surface is larger than the width of the band electrode. As such, according to certain preferred arrangements it is desirable that each boron doped diamond electrode has a length/width ratio of at least 10, 20, 30, 40, 50, 100, 500, 1000, 2000, 5000, or 8000 at the sensing surface.

The length/width ratio of the electrodes is typically equal to or less than 15000, 10000, 8000, 5000, 2000, or 1000. For instance, the length/width ratio may lie in a range 10 to 15000, 20 to 10000, 30 to 5000, or 50 to 1000.

In an embodiment, each boron doped diamond electrode may have a width of at least 0.1 μm, 0.5 μm, 1 μm, 2 μm, 5 μm, 10 μm, or 15 μm. The width of each electrode may be equal to or less than 100 μm, 80 μm, 60 μm, 40 μm, 20 μm, 10 μm, 3 μm, or 1 μm. For example, the width may lie in a range 0.1 to 100 μm, 1 to 80 μm, 5 to 60 μm, 10 to 40 μm, or 15 to 30 μm. For certain applications each boron doped diamond electrode may have a length of at least 100 μm, 200 μm, 400 μm, 600 μm, 800 μm, or 1000 μm. The surface area at the sensing surface of at least $0.0001\ mm^{-2}$, $0.001\ mm^{-2}$, $0.005\ mm^{-2}$, $0.010\ mm^{-2}$, $0.015\ mm^{-2}$, or $0.020\ mm^{-2}$.

The functional performance of the sensor may depend on the concentration and uniformity of boron dopant within the boron doped diamond electrodes. At least a portion of each boron doped diamond electrode may comprise a boron concentration equal to or greater than $1\times10^{20}\ cm^{-3}$, $2\times10^{20}\ cm^{-3}$, $4\times10^{20}\ cm^{-3}$, $5\times10^{20}\ cm^{-3}$, $7\times10^{20}\ cm^{-3}$, $1\times10^{21}\ cm^{-3}$, or $2\times10^{21}\ cm^{-3}$. Preferably, the concentration of boron varies by no more than 50%, 30%, 20%, 10%, or 5% of a mean concentration over at least 70% 80%, 90%, or 95% of the area of the boron doped diamond electrode at the sensing surface, at least for single crystal boron doped diamond electrodes.

For polycrystalline boron doped diamond electrodes, it has been found that only a portion of the material is required to be doped to a sufficient level to be metallically conductive. As such, for polycrystalline boron doped diamond electrodes only a portion of grains at an exposed working surface of each electrode are required to be metallically conductive having a boron content of at least $1\times10^{20}$ boron atoms $cm^{-3}$. The grains of the polycrystalline material may vary in orientation. In contrast, for single crystal boron doped diamond electrodes it is advantageous that substantially all the exposed working surface of each electrode is doped to such a level.

During operation, the electrochemical sensor may be introduced into an electrochemical cell. Condensate tested for conductivity may be analyzed when disposed in the housing of the electrochemical cell. The diamond sensor may be disposed in an electrochemical probe. Also provided in the electrochemical cell are a counter electrode and a reference electrode. These electrodes are typically connected to a controller for applying a potential to the electrodes and/or sensing a potential generated at the electrodes by an electrochemical reaction.

Furthermore, in use, the electrode may be in contact with fluid which is flowing, and which has a distinct flow direction. Generally the front sensor surface of the device will be oriented such that the flow direction lies substantially parallel to the front sensor surface, and if the front sensor surface is curved in the form of a cylinder then the flow direction lies parallel to the cylindrical axis. In some applications the orientation of the long axis of the electrodes may be at an arbitrary angle with respect to the flow direction. In others it may beneficial to orient the long axis of the electrodes substantially perpendicular to the flow direction, i.e. at >70°, 80°, 85° to the flow direction, and in other applications it may be beneficial to orient the long axis of the electrodes substantially parallel to the flow direction, i.e. <20°, 10°, 5° to the flow direction.

In addition to measuring conductivity, the boron doped diamond based electrochemical band sensor described herein may be used or, optionally, modified to measure oxidation reduction potential. Since oxidation reduction potential in aqueous based fluids is a measure of the tendency of the solution to either gain or lose electrons when it is subject to change by introduction of a new species, measurement of the oxidation reduction potential of the aqueous fluid may be used to monitor water quality in a steam generating system as well as in a hydrothermal liquefaction unit. The oxidation reduction potential may be defined relative to a reference electrode and the potential determined by measuring the potential difference between the boron doped diamond based electrochemical band sensor in contact with the fluid and a stable reference electrode connected to the solution by a salt bridge.

In another embodiment, the boron doped diamond based electrochemical band sensor may be modified in accordance with the teachings of the prior art to exist as a pH probe. The pH probe may be placed within the steam generating system to measure the acidity and alkalinity of the condensate. Since steam generating systems are designed to operate such that the condensate has a defined pH or pH range, deviations from the defined pH range are indicative of problems within the steam generating system. For instance, changes in acidity or alkalinity of the condensate may be indicative of excessive mineral scale, carbonic corrosion, and thermal fatigue.

Preferred embodiments of the present disclosure thus offer advantages over the prior art and are well adapted to carry out one or more of the objects of this disclosure. However, the present disclosure does not require each of the components and acts described above and are in no way limited to the above-described embodiments or methods of operation. Any one or more of the above components, features and processes may be employed in any suitable configuration without inclusion of other such components, features and processes.

Moreover, the present disclosure includes additional features, capabilities, functions, methods, uses and applications that have not been specifically addressed herein but are, or will become, apparent from the description herein and claims. The methods that may be described above or claimed herein and any other methods which may fall within the scope of the appended claims can be performed in any desired suitable order and are not necessarily limited to any sequence described herein or as may be listed in the appended claims. Further, the methods of the present disclosure do not necessarily require use of the particular embodiments shown and described herein, but are equally applicable with any other suitable structure, form and configuration of components.

While exemplary embodiments of the disclosure have been shown and described, many variations, modifications and/or changes of the system, apparatus and methods of the present disclosure, such as in the components, details of construction and operation, arrangement of parts and/or methods of use, are possible, contemplated by the patent applicant(s), within the scope of the appended claims, and may be made and used by one of ordinary skill in the art without departing from the spirit or teachings of the disclosure and scope of appended claims.

What is claimed is:

1. A method of monitoring conductivity in a steam generating system comprising:
   (a) contacting fluid flow in a steam generating system with a boron doped diamond based electrochemical band sensor, the boron doped diamond based electrochemical band sensor comprising a diamond body and a plurality of boron doped diamond band electrodes disposed within the diamond body, said sensor having a front surface adapted to be oriented with respect to the flow of the fluid; and
   (b) measuring the conductivity of the fluid at a temperature in excess of 900° F. by applying voltage to the boron doped diamond based electrochemical band sensor,
      wherein the steam generating system is either (a) a boiler system and the boron doped diamond based electrochemical band sensor is placed within the boiler or heat exchanger of the boiler system, or (b) a steam turbine.

2. The method of claim 1, wherein at least one of the following conditions exist:
   (a) the boron doped diamond based electrochemical band sensor is placed within a flash tank; or
   (b) the boron doped diamond based electrochemical band sensor is placed inside of a probe.

3. The method of claim 2, wherein the probe is placed inside a flash tank.

4. The method of claim 1, wherein the fluid is a condensate generated in the steam generating system.

5. The method of claim 1, wherein the steam generating system is a boiler.

6. The method of claim 5, wherein the boron doped diamond band sensor is used continuously during blowdown of water from the boiler.

7. The method of claim 5, wherein the boiler is in a petrochemical plant, oil refinery or a power generation station.

8. The method of claim 5, wherein the boiler is in a multi-unit residential facility.

9. The method of claim 5, wherein the boiler is in an educational facility.

10. A method of monitoring conductivity in real time in a steam generating system without interruption of the steam generating system, the method comprising:
    (a) contacting fluid flow in a steam generating system with a boron doped diamond based electrochemical band sensor, the boron doped diamond based electrochemical band sensor comprising a diamond body and a plurality of boron doped diamond band electrodes disposed within the diamond body, said sensor being curved in the form of a cylindrical surface and having a cylindrical axis capable of being oriented with the cylindrical axis substantially parallel with the flow direction of the fluid; and
    (b) measuring the conductivity of the fluid over time by applying voltage to the boron doped diamond based electrochemical band sensor.

11. The method of claim 10, wherein at least one of the following conditions exist:
    (a) when the steam generating system is a boiler system the boron doped diamond based electrochemical band sensor is placed within the boiler or heat exchanger of the boiler system; or
    (b) the boron doped diamond based electrochemical band sensor is placed within a flash tank; or
    (c) the boron doped diamond based electrochemical band sensor is placed inside of a probe.

12. The method of claim 11, wherein the probe is placed inside a flash tank.

13. The method of claim 10, wherein the fluid is a condensate generated in the steam generating system.

14. The method of claim 10, wherein the steam generating system is a boiler.

15. The method of claim 14, wherein the boron doped diamond band sensor is used continuously during blowdown of water from the boiler.

16. The method of claim 14, wherein the boiler is in a petrochemical plant, oil refinery or a power generation station.

17. The method of claim 14, wherein the boiler is in a multi-unit residential facility.

18. The method of claim 14, wherein the boiler is in an educational facility.

19. A method of monitoring conductivity in a steam generating system comprising:
  (a) contacting fluid flow in a steam generating system with a boron doped diamond based electrochemical band sensor, the boron doped diamond based electrochemical band sensor comprising a diamond body and a plurality of boron doped diamond band electrodes disposed within the diamond body, said sensor having a front surface adapted to be oriented with respect to the flow of the fluid; and
  (b) measuring the conductivity of the fluid at a temperature in excess of 900° F. by applying voltage to the boron doped diamond based electrochemical band sensor.

20. The method of claim 19, wherein at least one of the following conditions exist:
  (a) when the steam generating system is a boiler system the boron doped diamond based electrochemical band sensor is placed within the boiler or heat exchanger of the boiler system; or
  (b) the boron doped diamond based electrochemical band sensor is placed within a flash tank; or
  (c) the boron doped diamond based electrochemical band sensor is placed inside of a probe.

21. The method of claim 19, wherein the probe is placed inside a flash tank.

22. The method of claim 19, wherein the fluid is a condensate generated in the steam generating system.

23. The method of claim 19, wherein the steam generating system is a boiler.

24. The method of claim 23, wherein the boron doped diamond band sensor is used continuously during blowdown of water from the boiler.

25. The method of claim 23, wherein the boiler is in a petrochemical plant, oil refinery or a power generation station.

26. The method of claim 23, wherein the boiler is in a multi-unit residential facility.

27. The method of claim 23, wherein the boiler is in an educational facility.

* * * * *